United States Patent [19]

Niznik

[11] 4,160,088
[45] Jul. 3, 1979

[54] DIHYDROOXADIAZINONES AND METHOD FOR MAKING

[75] Inventor: George E. Niznik, Elnora, N.Y.

[73] Assignee: General Electric Company, Schenectady, N.Y.

[21] Appl. No.: 789,420

[22] Filed: Apr. 21, 1977

Related U.S. Application Data

[62] Division of Ser. No. 608,450, Aug. 28, 1975, Pat. No. 4,097,671.

[51] Int. Cl.$^2$ .......................................... C07D 273/04
[52] U.S. Cl. ..................................................... 544/68
[58] Field of Search ............................................ 544/68

[56] References Cited

U.S. PATENT DOCUMENTS

| | | | |
|---|---|---|---|
| 4,097,425 | 6/1978 | Niznik | 260/2.5 N |
| 4,097,671 | 6/1978 | Niznik | 544/68 |

OTHER PUBLICATIONS

Edwards et al., J. Chem. Soc., 1937, pp. 1942-1946.

Rosenblum et al., J. Am. Chem. Soc., vol. 85, pp. 3874-3878 (1963).
Blatt, Organic Syntheses, Collective vol. 2, pp. 480-481, John Wiley & Sons, Inc., NY (1943).
Weidenhagen et al., Ber. Deut. Chem., vol. 68, pp. 1953 & 1955 (1935).
Beilsteins Handbuch der Organishchen Chemie, 4th Ed., 3rd Supplement, 7th vol., 2nd part, pp. 967 & 979, Springer-Verlag, Berlin, Germany (1968).

Primary Examiner—John D. Randolph
Attorney, Agent, or Firm—William A. Teoli; Joseph T. Cohen; Charles T. Watts

[57] ABSTRACT

Dihydrooxadiazinones are provided which can be used as blowing agents in various thermoplastic polymeric materials to produce high performance thermoplastic foams. A ketone having at least one α-hydrogen atom is halogenated and hydroxylated to produce an α-hydroxyketone. Condensation of the α-hydroxyketone with an organocarbazate produces the corresponding carboorganooxyhydrazone which is cyclized to a dihydrooxadiazinone.

19 Claims, No Drawings

DIHYDROOXADIAZINONES AND METHOD FOR MAKING

This is a division, of application Ser. No. 608,450, filed Aug. 28, 1975, now U.S. Pat. No. 4,097,671 granted June 27, 1978.

The present invention relates to dihydrooxadiazinones, namely 3,6-dihydro-1,3,4-oxadiazin-2-ones, and a method for making such materials. There is also included by the present invention a method for halogenating certain ketones having α-hydrogen atoms and a method of hydroxylating certain α-halo ketones to produce the corresponding α-hydroxy ketone.

The dihydrooxadiazinones provided by the method of the present invention are included by the formula

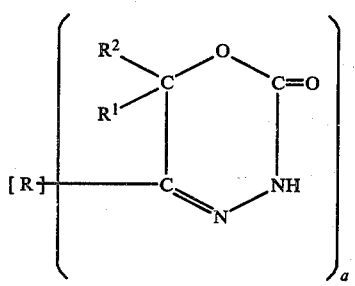

where "a" is an integer equal to 1 or 2, R is a monovalent radical when "a" is 1 and R is a divalent radical when "a" is 2, and R is selected from alkyl radicals and aryl radicals, alkylene and arylene radicals, and $R^1$ and $R^2$ are monovalent or divalent radicals which can be the same or different selected from hydrogen, alkyl, alkylene, or cyclo aliphatic ring structure including $R^1$ and $R^2$, alkoxy radicals and arloxy radicals, etc.

Radicals included by R of Formula 1 are $C_{(1-8)}$ alkyl radicals, such as methyl, ethyl, propyl, butyl, etc.; aryl radicals such as phenyl, tolyl, xylyl, napthyl, anthryl, etc.; $C_{(1-8)}$ alkylene radicals; phenylene, xylylene, etc.; halo alkyls such as chloroethyl, trifluoropropyl, etc.; halo aryls such as chlorophenyl, bromotolyl, etc.; nitro aryls and sulfoaryls. Radicals included by $R^1$ and $R^2$ are hydrogen, and $C_{(1-8)}$ alkyl radicals such as methyl, ethyl, propyl, etc.; alkoxy radicals such as methoxy, ethoxy, propoxy, butoxy, etc.; aryloxy radicals such as phenoxy, cresoxy, napthoxy, etc. In particular instances where $R^1$ and $R^2$ are both alkyl they can be part of a cycloaliphatic ring structure such as cyclopentyl, cyclohexyl, cycloheptyl.

As shown in my copending application, RD-8111, filed concurrently herewith and assigned to the same assignee as the present invention, the dihydrooxadiazinones of Formula 1 can be employed as blowing agents in a variety of thermoplastic organic polymers. Included by the dihydrooxadiazinones of Formula 1 are, for example, 5,6-dimethyl-3,6-dihydro-1,3,4-oxadiazin-2-one,
5,6,6-trimethyl-3,6-dihydro-1,3,4-oxadiazin-2-one,
5-ethyl-6-methoxy-3,6-dihydro-1,3,4-oxadiazin-2-one,
5,6-diphenyl-3,6-dihydro-1,3,4-oxadiazin-2-one,
5-(p-bromophenyl)-3,6-dihydro-1,3,4-oxadiazin-2-one,
5-phenyl-6-methyl-3,6-dihydro-1,3,4-oxadiazin-2-one,
5,6-bis(p-methoxyphenyl)-3,6-dihydro-1,3,4-oxadiazin-2-one,
5-napthyl-3,6-dihydro-1,3,4-oxadiazin-2-one,
5-(o,o,p-tribromophenyl)-6-propyl-3,6-dihydro-1,3,4-oxadiazin-2-one,
5-(p-hydroxyphenyl)-3,6-dihydro-1,3,4-oxadiazin-2-one,
5-phenyl-6,6-cyclopentylene-3,6-dihydro-1,3,4-oxadiazin-2-one, and such polycyclic formulas resulting from divalent substitution as

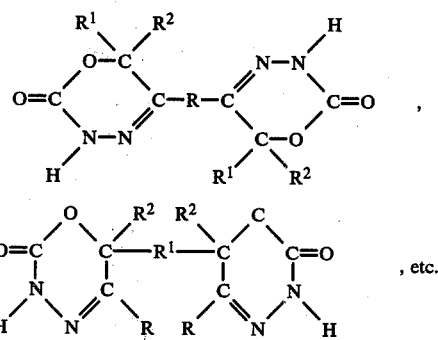

Also included by the present invention, are a particular class of dihydrooxadiazinones within the scope of Formula 1, and further shown by the following formula,

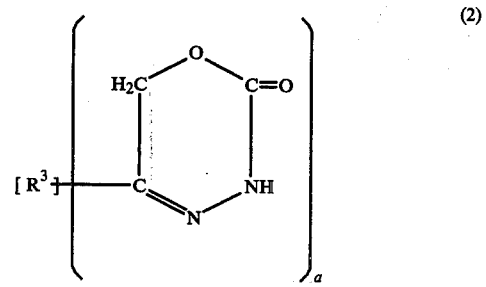

where $R^3$ is an aryl radical, arylene radical or substituted aryl radical, or substituted arylene radical, such as phenyl, phenylene, chlorophenyl, tolyl, sulphonated napththyl, etc. The dihydrooxadiazinones of Formula (2) are shown in my copending application, RD-8111, filed concurrently herewith and assigned to the same assignee as the present invention. Included by Formula 2 is 5-phenyl-3,6-dihydro-1,3,4-oxadiazin-2-one, which is especially useful as a high temperature blowing agent in thermoplastic organic polymers such as polycarbonates.

Based on prior art procedures, certain dihydrooxadiazinones can be made by the condensation of an α-ketol such as benzoin with equimolar quantites of carbethoxy hydrazine to produce a carbethoxy hydrazone followed by cyclization as shown by the following reaction sequence:

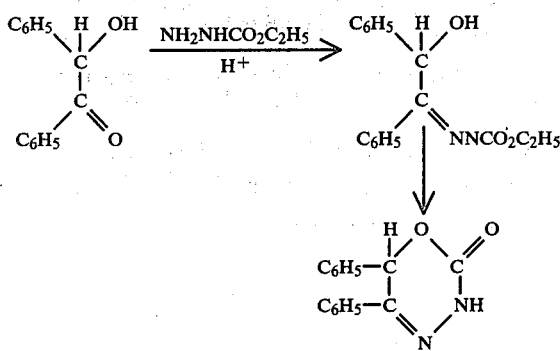

The synthesis and pyrolysis of dihydrooxadiazinones have been extensively reported by M. Rosenblum et al., Synthesis of Dihydrooxadiazinones and Study of Geometrical Isomerism in α-Ketolcarboxyhydrazones, Volume 85, P. 3874 (1963). J. Amer. Chem. Soc. In addition to discussing the use of oxadiazinones as research tools in pyrolysis studies, Rosenblum et al. show the synthesis of the dihydrooxadiazinones from α-ketols. Also described by Rosenblum et al. is the employment of a carbethoxy hydrazine to produce the corresponding carbethoxy hydrazone. The synthesis of the dihydrooxadiazinones by the aforementioned procedure of Rosenblum et al. is somewhat limited by the available α-ketols as source materials. Current procedures for making α-ketols are generally based on the hydroxylation of the corresponding α-halo ketone which is derived from a ketone possessing an α-hydrogen atom. However, the procedures available in the prior art are generally undesirable yield wise for both the synthesis of α-halo ketones and the hydroxylation of the α-halo ketones to the α-ketol.

One feature of the present invention, therefore, is directed to the production of α-halo ketones by the halogenation of ketones having α-hydrogen atoms. Prior to the present invention, halogenation of ketones containing α-hydrogen atoms was generally achieved by halogenating the ketone in the presence of a Lewis acid catalyst. Although this procedure was effective, it invariably resulted in the production of polyhalogenated products instead of the exclusive production of the monohalogenated product. A procedure is described by Cooper and Davidson, Org. Syn. Coll., Vol. 2, 480 (1943) showing the bromination of acetophenone in diethyl ether with aluminum chloride. At best, a mixture is obtained consisting of only 81.8 mole percent of the desired α-bromoacetophenone and 14.2 mole percent of polybrominated reaction products along with 4.1 mole percent of unreacted acetophenone. This mixture must be purified by recrystallisation which introduces a considerable loss in isolated yield. As a result, the overall economics of available bromination reactions renders these procedures undesirable.

One aspect of the present invention is based on the discovery that if a ketone containing at least two α-hydrogen atoms, as shown by the formula, $$R-\overset{O}{\underset{\|}{C}}-CH_2R^1 \quad (3)$$

is halogenated at a temperature in the range of between 0° C. to 50° C. in the presence of an effective amount of a mineral acid catalyst, and from 1 to 20 parts per part of said ketone of a $C_{(1-8)}$ aliphatic alcohol, that α-haloketone is formed substantially free of any polyhalogenated ketone.

There is provided by the present invention, therefore, a process for making an α-halo ketone based on the halogenation of a ketone of Formula 2, which prior to the present invention, resulted in the production of an α-halo ketone along with significant amounts of poly α-halogenated ketone, which is based on the improvement which comprises, (1) halogenating the ketone in the range of from 0° C. to 50° C. in the presence of an effective amount of a Lewis Acid catalyst, or mineral acid catalyst, along with from 1 to 20 parts per part of ketone of a $C_{(1-8)}$ aliphatic alcohol, (2) recovering from the mixture of (1), α-halo ketone substantially free of polyhalogenated ketone.

Included by the ketones of Formula (3) are, for example,
acetophenone
propiophenone
deoxybenzoin
p-bromoacetophenone
napthophenone
p-methoxyacetophenone
desoxyanisoin
diacetylbenzene
2,3-butanedione
2-acetylfluorene
p-acetylbenzenesulfonicacid
acetovanillane
α-acetylanthracene
p-hydroxypropiophenone
p-benzyloxypropiophenone
m-nitroacetophenone
3-(p-methoxybenzoyl)-propionicacid
2',4'-dihydroxy-α-(p-methoxyphenyl)-acetophenone
1,3,5-triacetylbenzene
3,4-dichloroacetophenone
1,4-dibenzoylbutane
β-chloropropiophenone
3-benzoyl-2-phenylpropionitrile
1,4-benzodioxan-6-yl methyl ketone In addition to providing a route to α-halo ketones, another aspect of the present invention is directed to the production of α-halo ketols based on the hydrolysis of α-halo ketone. Prior to the present invention, one of the methods for making an α-ketol, such as α-hydroxy acetophenone, involved the formation of the acetate derivative of α-bromo acetophenone, which produced by an acid catalyzed transesterification the α-hydroxy acetophenone in 45% overall yield. A further complication of the aforementioned acetate route is that high molecular weight byproducts formed during the hydroxylation have to be removed by a purification step. Efforts to directly hydrolyze α-halo ketones also presents some difficulty as those skilled in the art know that α-halo ketones are quite stable to hydrolysis in slightly acidic media unless the hydrolysis is assisted by silver ions. A procedure described by D. J. Lastow et al., J. Amer. Chem. Soc. 87, 1515 (1965) does not provide yields greater than 81% according to gas chromatographic analysis. Interfacial hydrolysis of α-halo ketones, such as α-bromo acetophenone with sodium hydroxide can result in the production of over 20 major products during the reaction. The substitution of a milder base such as sodium carbonate can provide yields as little as 10% of the desired α-ketol.

Another aspect of the present invention is based on the discovery that α-halo ketones can be readily converted to α-ketols by effecting the hydrolysis of the α-halo ketone in a water miscible organic solvent, such as acetonitrile, in the presence of an alkali metal salt buffer and an alkali metal salt carboxylic acid promotor such as sodium formate, resulting in quantitative yields of the desired α-ketol.

Accordingly, there is also provided by the present invention, a process for making an α-hydroxy ketone which comprises, (1) agitating at a temperature in the range of from about 25° C. to 85° C., a mixture containing as essential ingredients the following:
 (A) α-halo ketone
 (B) water miscible organic solvent
 (C) a buffer in the form of an alkali metal salt of a poly basic acid capable of maintaining the pH of the mixture between about 6.5 to 11
 (D) alkali metal salt of an organic carboxylic acid having a pKa of less than about 4
 (E) water where there is utilized per mole (A), at least one equivalent of alkali metal atoms of (C), at least 0.05 equivalents of alkali metal atoms of (D), and per part of (A), at least one part of (B), and (B) and (E) are employed in the mixture in an amount which is at least sufficient to provide an equivalent of OH, per halogen atoms of (A), while maintaining a ratio of (B)/(E) having a value of between 0.2 to 8.0, (2) recovering α-hydroxy ketone from the resulting mixture of (1).

The dihydrooxadiazinones of Formula 1 can be made in accordance with the practice of the present invention by the following reaction sequence:

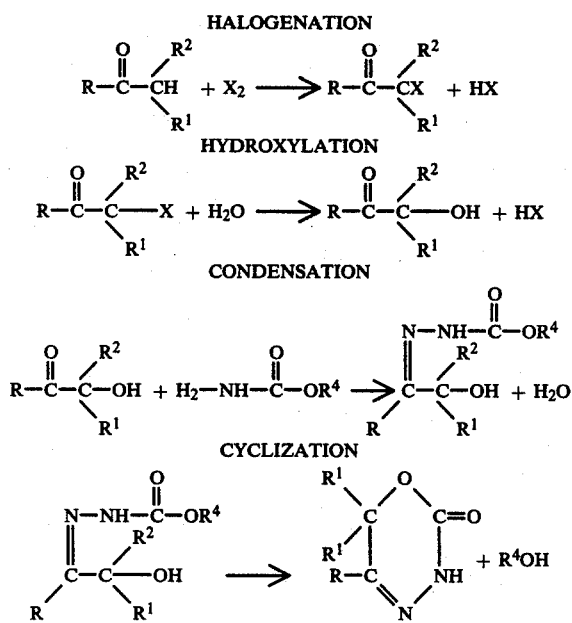

There is provided by the present invention, therefore, a method for making a dihydrooxadiazinone which comprises, (1) halogenating a ketone having at least one α-halogen atom at a temperature in the range of from 0° C. to 50° C. in the presence of an effective amount of a mineral acid catalyst or a Lewis Acid catalyst and from 1 to 20 parts per mole of said ketone of a $C_{(1-8)}$ aliphatic alcohol, (2) recovering an α-halo ketone from the mixture of (1), (3) hydrolyzing the α-halo ketone of (2) by agitating a mixture at a temperature in the range of from 25° C. to 85° C. containing the following as essential ingredients,
 (A) α-halo ketones
 (B) water miscible organic solvent,
 (C) a buffer in the form of an alkali metal salt of a poly basic mineral acid capable of maintaining the pH of the mixture in the range of between 6.5 to 11,
 (D) alkali metal salt of an organic carboxylic acid having a pKa less than 4,
 (E) water, (4) effecting reaction between the resulting α-hydroxy ketone of (3) and an organocarbazate to produce a carbonoorganooxyhydrazone, and (5) effecting cyclization of the carbonoorganooxyhydrazone in the presence of an organic solvent to produce a dihydrooxadiazinone.

In the practice of the invention, a ketone having an α-hydrogen atom is halogenated to convert it to α-halo ketone. The α-halo ketone is thereafter hydroxylated to produce an α-ketol. The α-ketol is condensed with an organo carbazate to produce a carboalkoxyhydrazone which is cyclized to a dihydrooxadiazinone.

The halogenation of α-hydro ketone is effected by initially forming a mixture of the ketone and the alkanol. Although methanol is preferred, suitable alkanols which can also be used are ethanol, propanol, butanol, pentanol, etc. Halogenation of the ketone-alkanol mixture can be initiated by introducing a small portion of the halogen followed by the introduction of the acid catalyst. During this period, the mixture is stirred and maintained at a temperature in the range of from 0° C. to 50° C. Suitable acid catalysts which can be used are, for example, hydrogen chloride, hydrogen bromide, sulfuric acid, etc., or Lewis Acid catalysts such as boron trifluoride, aluminum chloride, iron chloride, antimony hexafluoride, tin chloride, etc. The catalysts can be employed in an amount which can vary from 0.1% to 5% based on the weight of ketone. The balance of the halogenating reagent such as bromine can then be added. Halgenation can be achieved over a period of from 1.5 to 24 hours depending upon the nature of the halogen employed, the temperature of the mixture and the reactants used, etc. It has been found that if substantially equal molar amounts of halogen and ketone are used, effective results can be achieved. However, from 0.95 moles to 1.05 moles of halogen, per mole of ketone also can be employed without adversely affecting the overall yield of the reaction.

Prior to recovering the resulting α-halo ketone, it has been found desirable to introduce into the mixture, a small amount of water to minimize the contamination of the product with enol ethers. Based on the moles of halogen used in the mixture, there can be introduced up to 10 mole percent of water at the termination of the halogenation reaction to minimize enol formation. Partial crystallization of the product can occur during the initial introduction of water. After the mixture has been cooled to a temperature usually in the range of between about 0° to 25° C., excess water can be added to effect the separation of the α-halogenated ketone which may be in the form of crystals or a liquid depending upon the ketone used. Recovery of the α-halo ketone can then be effected by standard means such as filtration, centrifugation, etc. In addition to bromination, additional means of halogenating the ketones used in the practice of the present invention are for example, chlorination, iodination.

Ketone halogenation can be effectively achieved by the employment of a mineral acid catalyst which can be introduced simultaneously or following the introduction of halogen into the mixture of ketone and aliphatic alcohol.

At the termination of the halogenation reaction, up to about 10 mole percent of water based on the moles of halogen employed can be initially introduced which can cause a small degree of precipitation of the α-halo ketone. The mixture can then be continuously stirred or agitated by standard means for a period of 10 to 60 minutes to minimize the production of enol ethers which can interfere with the purity of the final α-halo ketone. An excess of water then can be added to the mixture amounting to 150% to 800% by weight, based on the weight of the mixture to effect the precipitation of the α-halo ketone. Recovery of the final product can be effected by standard means such as by filtration, decantation, etc.

In preparing the α-hydroxy ketone, experience has shown that the order of addition of the various reactants is not critical. Accordingly a mixture of the α-halo ketone with the water miscible solvent, and the "promotor" which hereinafter will refer to an alkali metal salt of a organic carboxylic acid, such as sodium formate can be initially agitated. Water and the alkali metal salt of a polybasic acid can be added, and the total agitated from a period of from 2 to 60 hours at a temperature in the range of between about 25° C. to 85° C. Upon allowing the mixture to cool to a temperature of 10° C. to 30° C., separation of the α-hydroxy ketone can be readily effected. Recovery of the product depending upon whether it is a solid or a liquid, can be achieved by standard techniques. If desired, further purification of the product, such as recrystallization can be effected.

By combining the above-described halogenation step and hydrolysis step, with a subsequent condensation and cyclization step, a total synthesis of the dihydrooxadiazinones of the present invention can be achieved from a starting ketone containing an α-hydrogen atom by further condensing the α-hydroxy ketone with an organocarbazate followed by the cyclization of the resulting carboorganooxyhydrazone to the dihydrooxadiazinone. The organo carbazate used in the condensation step can include for example, methyl carbazate, ethyl carbazate, phenyl carbazate, isopropyl carbazate, butyl or isobutyl carbazate, ethylenebiscarbazate, phenylenebiscarbazate, etc. The condensation can be effected at temperatures in the range of between about 20° C. to 60° C. Substantially equal molar amounts of the α-hydroxy ketone, which can exist in solution from the above hydrolysis reaction and the organo carbazate can be stirred when the mixture is maintained at a pH of about 4 to 6 which can be achieved by adding to the mixture a mineral acid such as hydrochloric acid or sulfuric acid. The condensation reaction can be effected at a temperature of from 20° C. to 60° C. over a period of from about 2 to 24 hours. Recovery of the carboorganooxyhydrazone can be effected by gravity separation techniques such as filtration, etc., and the product washed with water and dried by standard means.

The cyclization of the carbooorganooxyhydrazone can be achieved by heating it with an organic solvent such as toluene. There can be added a cyclization catalyst such as anhydrous potassium carbonate, sodium carbonate, sodium hydride, sodium alkoxide, etc. The dihydrooxadiazinone can be recovered by allowing the mixture to cool thereafter washing the final product with an organic solvent or hot water and drying by standard means such as a vacuum oven at temperatures in the range of about 70°-80° C. It has been found as a practice that the carboorganooxyhydrazone can be dried by azeotropic distillation under reduced pressure prior to the addition of the cyclization catalyst.

The dihydrooxadiazinones which can be made in accordance with the practice of the present invention, can be used as blowing agents in a variety of thermoplastic organic polymers as shown in my copending application, RD-8111 filed concurrently herewith and assigned to the assignee of the present invention. A proportion of from about 0.1 to 1.0 percent of blowing agent, based on the weight of the plastic will provide for effective results. Incorporation can be achieved by standard melt extrusion techniques based on the particular decomposition point of the blowing agent and the melt extrusion characteristics of the thermoplastic polymer.

In order that those skilled in the art will be better able to practice the invention, the following examples are given by way of illustration and not by way of limitation. All parts are by weight.

EXAMPLE 1

There was added 5 parts of bromine to a mixture of 120.15 parts of acetophenone and 190 parts of methanol, which was being stirred during the addition. The temperature of the mixture was maintained at about 10°-15° C.; anhydrous hydrogen bromide was then introduced into the reaction solution until the bromine color disappeared. An additional amount of bromine was then introduced over a 2 hour period to produce a mixture to which an equal molar amount of bromine per mole of acetophenone had been added. After the bromine had been added, 18 parts of water was introduced which amounted to about 100 mole percent of water based on the moles of bromine added. The reaction mixture was then cooled to a temperature of from 0° C.–15° C. An excess of water amounting to about 1300 parts was then added over a 15 minute period with stirring to effect the precipitation of α-bromo acetophenone which separated as fine white crystals. The crystals were collected on a filter paper and rinsed with water. Based on weight of reactants the yield of product was about 96% having a purity of greater than 99.9%.

EXAMPLES 2-6

The procedure of Example 1 involving halogenating with bromine was repeated except that in particular instances the alcohol used was varied or the ketone was varied. The results shown are as follows:

TABLE I

| Example | Alcohol | Ketone | % Yield(isolated) |
| --- | --- | --- | --- |
| 2 | methanol | deoxybenzoin | >95 |
| 3 | methanol | propiophenone | >95 |
| 4 | ethanol | acetophenone | 98 |
| 5 | isopropyl | acetophenone | >95 |
| 6 | methanol | p-bromoacetophenone | 95 |

The procedure of Examples 1–6 was repeated except that in place of $C_{(1-8)}$ aliphatic alcohol there was used acetonitrile as the solvent. The temperature of the mixture was maintained between 0° to 5° C. during the bromination. There was obtained a mixture containing about a 67% of α-bromo acetophenone which was significantly less than the quantitative yield achieved by use of a $C_{(1-8)}$ aliphatic alcohol in accordance with the practice of the present invention. In addition to acetonitrile, acetic acid and methylene chloride were used as substitution for the $C_{(1-8)}$ alcohol at the same or substantially the same molar concentration as employed in Examples 1–6 above. The α-bromo acetophenone obtained at 0° to 5° C. with acetic acid was about 61.6% and that obtained with methylene chloride was about 67.8%. Based upon these results, one skilled in the art would know that the results achieved by the use of a $C_{(1-8)}$ aliphatic alcohol were quite unexpected with respect to yield of α-halogenated ketone.

EXAMPLE 7

There was added 151.9 parts of sodium bicarbonate and about 600 parts of water to a mixture at a temperature of 50° C. while it was stirred of 300 parts of α-bromo acetophenone, 104.5 parts of sodium formate and about 700 parts of acetonitrile. The resulting mixture was stirred vigorously for 16 hours at 60° C. during which time carbon dioxide evolved. After cooling the reaction mixture, the acetonitrile solution was separated from the aqueous layer and evaporated to dryness to produce 97.5% of a crystalline product. The material was further purified by recrystallization from water resulting in the production of α-hydroxy acetophenone hydrate having a melting point in the range of 73°–76° C. The final yield of the isolated product was 72.5%.

Further studies were made on the hydrolysis of α-bromo acetophenone employing the method of Example 7, except that in certain instances the amount of sodium formate was varied or prepared in situ or the amount of sodium bicarbonate in acetonitrile were varied. Acetonitrile was varied over a range of from about 0.3 moles per liter up to about 0.9 moles per liter of reaction mixture. In addition to sodium bicarbonate, sodium carbonate was also used as an acid acceptor. The results obtained are shown as follows in Table II covering Examples 8–14 where percent yields of α-hydroxy acetophenone hydrate are based on peak areas using gas chromatographic analysis.

TABLE II

| Ex. | Solvent | Acid Acceptor (equiv.) | Promotor (equiv.) | %Yield |
| --- | --- | --- | --- | --- |
| 8 | acetonitrile | $Na_2CO_3$ (1.0) | — | 27 |
| 9 | acetonitrile | $NaHCO_3$ (1.2) | — | 81.4 |
| 10 | acetonitrile | $NaHCO_3$ (1.3) | $HCO_2Na$ (1.03) | >99.9 |
| 11 | acetonitrile | $NaHCO_3$ (2.0) | $HCO_2Na$ (0.1) | 88 |
| 12 | acetonitrile | $NaHCO_3$ (1.6) | $HCO_2H$ (0.25) | 99 |
| 13 | acetonitrile | $NaHCO_3$ (2.0) | $HCO_2H$ (0.4) | 99.3 |
| 14 | methanol | $NaHCO_3$ (1.2) | $HCO_2Na$ (1.0) | 97.5 |

Examples 8–14, above, indicate that an unexpected effect is achieved by the use of sodium formate as a promoter either as a salt or prepared in situ. The temperature of the reaction using sodium carbonate as an acceptor was 45° whereas results shown for sodium bicarbonate are based on a reaction temperature of 60°–65°. A significant result is also shown with respect to the amount of sodium formate used based on its equivalence present in the mixture and the percent yield of the α-hydroxyacetophenone.

EXAMPLE 15

There was added 10.08 parts of sodium bicarbonate and about 60 parts of water to a mixture of 21.3 parts of α-bromopropiophenone, 6.8 parts of sodium formate and about 90 parts of acetonitrile. The resulting mixture was stirred vigorously for 48 hours at 65° C. during which time carbon dioxide evolved. After cooling, the acetonitrile solution was separated from the aqueous layer and evaporated to dryness. The residue was dissolved into chloroform which was extracted once with water, dried over sodium sulfate, and evaporated to produce analytically pure (>98%) α-hydroxypropiophenone. The yield of this isolated product was 77.1%.

EXAMPLE 16

About 13 parts of bromine was added with stirring to a mixture of 474.6 parts of acetophenone in about 640 parts of methanol, while the mixture was stirred and maintained at a temperature between 5°–10° C. Hydrogen bromide gas was then introduced into the mixture until bromine coloration disappeared, at which point an additional amount of bromine was added over a 2 hour period to make a total of 631.3 parts. There was then added 71 parts of water while the mixture was stirred and externally cooled for a period of about 30 minutes. An excess of about 2700 parts of water was then slowly added to effect the precipitation in the form of crystals of α-bromo acetophenone from the mixture. The crystals were decanted by means of a vacuum siphon, washed, then neutralized with a 20% sodium hydroxide solution and decanted to dryness. There was then added about 940 parts water, 1600 parts of methanol, 333 parts of sodium bicarbonate and a sodium formate solution prepared from 161 parts of a 90% formic acid and sufficient sodium hydroxide to neutralize the acid. The mixture was heated at 60° C. with vigorous stirring for 7 hours after which time it was cooled to ambient temperature and filtered. Based on method of preparation and gas chromatographic analysis of the mixture there was produced α-hydroxy acetophenone in quantitative yields.

Dilute hydrochloric acid was added to the mixture of the above filtrate with 855.8 parts of methyl carbazate which had been prepared from equivalent amounts of hydrazine and dimethyl carbonate. Sufficient hydrochloric acid was used to provide a pH of 5.5 after which the mixture was stirred at 38° C. for 6 hours. A crystalline precipitate was formed which was filtered from the mixture and washed with water. Based on method of preparation and spectroscopic analysis the product was the carbomethoxy hydrazone of α-hydroxy acetophenone.

A mixture of the above carbomethoxyhydrazone and about 1,900 parts of toluene was refluxed under reduced pressure to effect the removal of residual water from the crystalline product. There was then added 10 parts of anhydrous potassium carbonate to the mixture and the heating was continued under reduced pressure until all the methanol-toluene azeotrope was removed. The mixture was then allowed to cool to produce the above-described blowing agent 5-phenyl-3,6-dihydro-1,3,4-dihydrooxidiazin-2-one which was finally dried in a vacuum oven at 70°–80° C. The overall yield of final product was 456 parts which represented a 65.5% yield based on acetophenone. The melting point of the product was 163°–165° C.

Dry powder blends of a bis-phenol-A polycarbonate resin powder having an intrinsic viscosity on the average of about 0.55 dl/g and a density of about 1.17 with the above described blowing agent of the present invention and a commercially available blowing agent isopropyl hydrazo dicarboxylate were prepared consisting respectively of 0.6 part of blowing agent per 100 part of the polycarbonate resin. The polycarbonate resin was in the form of a finely divided powder which had been dried at 125° C. for 16 hours. The aforementioned blends were melt extruded at temperatures in the range of from about 282° C. to 305° C. During melt extrusion thermoplastic foam was formed from the aforementioned finely divided dry blends. In addition to melt extruding the aforementioned foamable blends there was also melt extruded the same polycarbonate resin free of blowing agent. The density (g/cc) of the respective blends and the resin free of the blend was measured over the range of between 282° C. to 305° C. The intrinsic viscosity of the polycarbonate resin and the intrinsic viscosity in chloroform of the polycarbonate resin and the aforementioned blends was also measured over the range of between 282° C. to 322° C. to determine the reduction in molecular weight if any during the foaming process as a result of polymer degradation. The following table shows the result obtained, where "T" is in °C., "Density" shows the change effected over a temperature as a result of "foaming," "IV" shows the change in intrinsic viscosity if any, of the polycarbonate resin as a result of polymer degradation due to byproducts of the blowing agent, where Blend A contains the dihydrooxidiazinone in accordance with the present invention and Blend B contains the isopropyl hydrazo-dicarboxylate:

TABLE I

| | Density | | |
|---|---|---|---|
| T(°C.) | Polycarbonate | Blend A | Blend B |
| 282 | 1.17 | 1.18 | 1.15 |
| 293 | — | 1.03 | 0.82 |
| 299 | — | — | 0.80 |
| 305 | 1.13 | .86 | 0.70 |
| 316 | 1.14 | — | — |
| 321 | | | |

| | IV | | |
|---|---|---|---|
| T(°C.) | Polycarbonate | Blend A | Blend B |
| 282 | 0.57 | 0.57 | 0.55 |
| 293 | 0.56 | 0.57 | — |
| 299 | — | — | 0.48 |
| 305 | 0.54 | 0.53 | 0.46 |
| 316 | 0.54 | — | — |
| 321 | 0.52 | — | — |

The above results show that the molding temperature of the dihydrooxidiazinone of the present invention Blend A is somewhat higher than the molding temperature of the isopropylhydrazodicarboxylate Blend B. More significant, however, is the showing that the blowing agent of the present invention does not significantly change the intrinsic viscosity of the polycarbonate as the result of the foaming action. The isopropylhydrazodicarboxylate of the prior art shows a 15% change in the intrinsic viscosity of the polymer indicating that significant polymer degradation has occurred.

Although the above examples are limited to only a few of the very many variables included by the method of the present invention as well as the dihydrooxadiazinones, it should be understood that the present invention includes the parameters shown in the description preceding these examples as well as dihydrooxadiazinones as shown by formula (2).

What I claim as new and desire to secure by Letters Patent of the United States is:

1. In the process for making an $\alpha$-halo ketone involving the halogenation of an $\alpha$-dihydro ketone in the presence of an effective amount of a mineral acid catalyst or a Lewis Acid catalyst resulting in the production of the $\alpha$-halo ketone along with significant amounts of poly $\alpha$-halogenated ketone, the improvement which comprises halogenating the $\alpha$-dihydro ketone in the range of from 0° C. to 50° C. in the presence of the Lewis Acid catalyst or mineral acid catalyst along with from 1 to 20 parts, per part of the ketone of a $C_{(1-8)}$ aliphatic alcohol, to provide for the recovery of $\alpha$-halo ketone substantially free of poly $\alpha$-halogenated ketone.

2. Process as in claim 1, where the aliphatic alcohol is methanol.

3. Process as in claim 1, where the ketone is brominated.

4. Process as in claim 1, wherein the mineral acid catalyst is sulfuric acid or hydrogen bromide.

5. Process as in claim 1, where the aliphatic alcohol is ethanol.

6. Process as in claim 1, where the ketone is acetophenone.

7. Process as in claim 1, where the ketone is deoxybenzoin.

8. Process as in claim 1, where the ketone is propiophenone.

9. Process as in claim 1, where the ketone is p-bromoacetophenone.

10. A process for making $\alpha$-bromoacetophenone which comprises
   (1) agitating a mixture at 0° to 30° C. of substantial equal molar amounts of acetophenone and bromine in the presence of 1 to 20 parts of a $C_{(1-8)}$ aliphatic alcohol and an effective amount of a mineral acid or Lewis Acid catalyst.
   (2) adding with agitation 0.5 to 10 mole percent of water to the mixture based on the moles of bromine initially used in (1),
   (3) adding an additional excess of water to the mixture while agitating which is sufficient to effect the separation of the $\alpha$-bromoacetophenone as a crystalline product.

11. A method in accordance with claim 10, where the $C_{(1-8)}$ aliphatic alcohol is methanol.

12. A method in accordance with claim 10, where the mineral acid is hydrogen bromide or sulfuric acid.

13. A method in accordance with claim 10, where the temperature is maintained between 0°–15° C.

14. A process for making an $\alpha$-hydroxy ketone which comprises,
   (1) agitating at a temperature in the range of from about 25° C. to 85° C., a mixture containing as essential ingredients the following:
      (A) $\alpha$-halo ketone
      (B) water miscible organic solvent
      (C) a buffer in the form of sodium bicarbonate
      (D) sodium formate
      (E) water,
   where there is utilized per mole (A), at least one equivalent of sodium atoms of (C), at least 0.05 equivalents of sodium atoms of (D), and per part of (A), at least one part of (B), and (B) and (E) are employed in the mixture in an amount which is at least sufficient to provide an equivalent of OH, per halogen atom of (A), while maintaining a ratio of (B)/(E) having a value of between 0.2 to 8.0.

15. A method in accordance with claim 14, where the α-halo ketone is α-bromoacetophenone.

16. A method in accordance with claim 14, where the water miscible organic solvent is acetonitrile.

17. A method in accordance with claim 14, where the water miscible organic solvent is methanol.

18. A method for making α-hydroxy acetophenone which comprises,
    (1) agitating at a temperature in the range of from 40° to 70° C. a mixture containing the following as essential ingredients,
        (A) α-Bromoacetophenone
        (B) acetonitrile (or methanol)
        (C) sodium bicarbonate
        (D) sodium formate
        (E) water
    where there is utilized per mole of (A), from about 1 to 2 equivalents of sodium atoms of (C), from about 0.25 to 1 equivalents of sodium atoms of (D), and per part of (A), at least one part of (B), and (B) and (E) are employed in the mixture in an amount which is at least sufficient to provide an equivalent of OH, per halogen atom of (A) while maintaining a ratio of (B)/(E) having a value of between 0.4 to 4.0.
    (2) recovering α-hydroxy ketone from the resulting mixture of (1).

19. A method for making a dihydrooxadiazinone which comprises,
    (1) halogenating a ketone having at least one α-hydrogen atom at a temperature in the range of from 0° C. to 50° C. in the presence of an effective amount of a mineral acid catalyst or a Lewis Acid catalyst and from 1 to 20 parts per part of said ketone of a $C_{(1-8)}$ aliphatic alcohol,
    (2) recovering an α-halo ketone from the mixture of (1)
    (3) hydrolyzing the α-halo ketone of (2) by agitating a mixture at a temperature in the range of from 25° C. to 85° C. containing the following as essential ingredients
        (A) α-halo ketones,
        (B) water miscible organic solvent,
        (C) sodium bicarbonate,
        (D) sodium formate,
        (E) water
    (4) utilizing the resulting mixture of (3) for (5),
    (5) effecting reaction between the α-hydroxy ketone and an organocarbazate to product a carboorganooxyhydrazone, and
    (6) effecting cyclization of the α-hydroxycarboorganooxyhydrazone in the presence of a basic catalyst and an organic solvent to produce a dihydrooxadiazinone.

* * * * *